(12) United States Patent
Shibata

(10) Patent No.: US 11,948,675 B2
(45) Date of Patent: *Apr. 2, 2024

(54) VIDEO SIGNAL GENERATING APPARATUS, VIDEO SIGNAL RECEIVING APPARATUS, AND VIDEO SIGNAL GENERATING AND RECEIVING SYSTEM

(71) Applicant: Sony Group Corporation, Tokyo (JP)

(72) Inventor: Yoshiaki Shibata, Kanagawa (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/351,255

(22) Filed: Jun. 18, 2021

(65) Prior Publication Data
US 2021/0313044 A1 Oct. 7, 2021

Related U.S. Application Data

(63) Continuation of application No. 16/459,327, filed on Jul. 1, 2019, now Pat. No. 11,056,226, which is a
(Continued)

(30) Foreign Application Priority Data

Sep. 12, 2006 (JP) ................. 2006-247179

(51) Int. Cl.
*G16H 30/20* (2018.01)
*G06T 7/00* (2017.01)
(Continued)

(52) U.S. Cl.
CPC .......... *G16H 30/20* (2018.01); *G06T 7/0012* (2013.01); *G11B 27/034* (2013.01);
(Continued)

(58) Field of Classification Search
CPC ........ G16H 30/20; G16H 30/40; G16H 50/20; G06T 7/0012; G06T 2207/10068;
(Continued)

(56) References Cited

U.S. PATENT DOCUMENTS

| 4,652,944 A | 3/1987 | Tindall |
| 5,701,153 A | 12/1997 | Reichek et al. |

(Continued)

FOREIGN PATENT DOCUMENTS

| JP | 04365278 A | 12/1992 |
| JP | 5-292447 | 11/1993 |

(Continued)

OTHER PUBLICATIONS

Yoshiaki Shibata, et al., "Essence Mark SMPTE Standard-based Textual Video Marker", SMPTE Motion Imaging Journal, Dec. 2005, pp. 463-473.

*Primary Examiner* — Girumsew Wendmagegn
(74) *Attorney, Agent, or Firm* — XSENSUS LLP

(57) ABSTRACT

A video signal generating apparatus is disclosed which includes: a camera configured to generate a video signal; an operating device configured to operate at least either the camera or an apparatus configured to receive the video signal; a text data generating device configured to generate text data including a meaningful term in response to the operation performed on the operating device; and a text data inserting device configured to insert the text data generated by the text data generating device into the video signal in a corresponding manner.

20 Claims, 9 Drawing Sheets

Related U.S. Application Data continuation of application No. 14/839,305, filed on Aug. 28, 2015, now Pat. No. 10,389,926, which is a continuation of application No. 11/834,167, filed on Aug. 6, 2007, now Pat. No. 9,153,284.

(51) Int. Cl.

| | | |
|---|---|---|
| *G11B 27/034* | (2006.01) | |
| *G11B 27/10* | (2006.01) | |
| *G11B 27/30* | (2006.01) | |
| *G16H 30/40* | (2018.01) | |
| *H04N 5/85* | (2006.01) | |
| *H04N 23/56* | (2023.01) | |
| *A61B 1/00* | (2006.01) | |
| *A61B 1/05* | (2006.01) | |
| *A61B 1/06* | (2006.01) | |
| *G06F 13/38* | (2006.01) | |
| *H04N 23/50* | (2023.01) | |

(52) U.S. Cl.
CPC ........ *G11B 27/105* (2013.01); *G11B 27/3027* (2013.01); *G16H 30/40* (2018.01); *H04N 5/85* (2013.01); *H04N 23/56* (2023.01); *A61B 1/00059* (2013.01); *A61B 1/05* (2013.01); *A61B 1/06* (2013.01); *G06F 13/385* (2013.01); *G06T 2207/10068* (2013.01); *H04N 23/555* (2023.01)

(58) Field of Classification Search
CPC ............... H04N 5/2256; H04N 5/85; H04N 2005/2255; G11B 27/105; G11B 27/3027; G11B 27/034; A61B 1/06; A61B 1/00059; A61B 1/05; G06F 13/385
See application file for complete search history.

(56) References Cited

U.S. PATENT DOCUMENTS

| | | | |
|---|---|---|---|
| 5,926,568 A * | 7/1999 | Chaney | G06V 10/754 |
| | | | 382/128 |
| 6,285,819 B1 | 9/2001 | Jeong | |
| 6,573,907 B1 | 6/2003 | Madrane | |
| 6,678,465 B1 * | 1/2004 | Swan | H04N 21/835 |
| | | | 386/257 |
| 7,071,942 B2 | 7/2006 | Zaima et al. | |
| 7,321,673 B2 | 1/2008 | Watai et al. | |
| 7,646,415 B2 | 1/2010 | Sugimoto | |
| 8,015,242 B2 | 9/2011 | Ohi et al. | |
| 8,443,279 B1 * | 5/2013 | Hameed | G06F 16/7867 |
| | | | 715/201 |
| 9,153,284 B2 | 10/2015 | Shibata | |
| 2002/0051575 A1 | 5/2002 | Myers et al. | |
| 2002/0078446 A1 | 6/2002 | Dakss et al. | |
| 2002/0139920 A1 | 10/2002 | Seibel | |
| 2003/0071893 A1 | 4/2003 | Miller | |
| 2003/0128400 A1 * | 7/2003 | Watai | G16H 30/20 |
| | | | 382/128 |
| 2004/0017996 A1 | 1/2004 | Yamaguchi | |
| 2004/0057697 A1 | 3/2004 | Renzi | |
| 2004/0122716 A1 | 6/2004 | Yogesan | |
| 2006/0053471 A1 * | 3/2006 | Walker | H04N 21/4367 |
| | | | 725/135 |
| 2006/0079752 A1 | 4/2006 | Andert | |
| 2006/0173859 A1 | 8/2006 | Kim et al. | |
| 2006/0177114 A1 | 8/2006 | Tongdee et al. | |
| 2006/0210254 A1 | 9/2006 | Yamashita et al. | |
| 2006/0253552 A1 * | 11/2006 | Ohi | H04N 19/86 |
| | | | 709/219 |

FOREIGN PATENT DOCUMENTS

| | | |
|---|---|---|
| JP | 2003-299010 | 10/2003 |
| JP | 2004-180279 | 6/2004 |
| JP | 2006-60732 | 3/2006 |
| JP | 2006-221583 | 8/2006 |
| JP | 2006-223357 | 8/2006 |

* cited by examiner

FIG. 1

| KEY | LENGTH | VALUE |
|---|---|---|
| (16 BYTES) | (≥1 BYTE) | (NO. OF BYTES INDICATED BY "LENGTH") |

FIG. 2

| RESERVED WORDS | DESCRIPTION |
|---|---|
| _RecStart | RECORDING START POINT OF AV MATERIAL |
| _RecEnd | RECORDING END POINT OF AV MATERIAL |
| _ShotMark1 | POINT OF INTERST 1 |
| _ShotMark2 | POINT OF INTERST 2 |
| _Cut | CUT POINT |
| _Flash | FLASHING LIGHT DETECTION POINT |
| _FilterChange | FILTER CHANGE POINT |
| _ShutterSpeedChange | SHUTTER SPEED CHANGE POINT |
| _GainChange | GAIN CHANGE POINT |
| _WhiteBalanceChange | WHITE BALANCE CHANGE POINT |
| _OverBrightness | POINT AT WHICH VIDEO SIGNAL OUTPUT LEVEL EXCEEDS 100% |
| _OverAudioLimiter | POINT AT WHICH AUDIO SIGNAL OUTPUT LEVEL EXCEEDS PREDETERMINED THRESHOLD |
| _In-XXX | IN-POINT (XXX : ANY CHARACTER STRING) |
| _Out-XXX | OUT-POINT (XXX : ANY CHARACTER STRING) |
| _KeyFrame | KEY FRAME |

```
< EssenceMarkTable targetMedia="Clip 1">
   <EssenceMark value="REC Start"timecode="00:00:00:00"/>
   <EssenceMark value="Top 2nd inning"timecode="00:02:25:04"/>
   <EssenceMark value="Ichiro at batter box"timecode="00:05:12:13"/>
   <EssenceMark value="Ichiro homerun"timecode="00:11:23:05"/>
        :
</EssenceMarkTable>
```

VIDEO SIGNAL GENERATING APPARATUS, VIDEO SIGNAL RECEIVING APPARATUS, AND VIDEO SIGNAL GENERATING AND RECEIVING SYSTEM

CROSS REFERENCES TO RELATED APPLICATIONS

The present application is a continuation of U.S. application Ser. No. 16/459,327, filed Jul. 1, 2019, which is a continuation of U.S. application Ser. No. 14/839,305, filed Aug. 28, 2015 (now U.S. Pat. No. 10,389,926), which is a continuation of U.S. application Ser. No. 11/834,167, filed Aug. 6, 2007 (now U.S. Pat. No. 9,153,284), which claims priority to JP 2006-247179, filed Sep. 12, 2006, the entire contents of each are incorporated herein by reference.

BACKGROUND OF THE INVENTION

1. Field of the Invention

The present invention relates to a video signal generating apparatus equipped with a camera and to a video signal receiving apparatus for receiving the video signal generated by that video signal generating apparatus. More particularly, the invention relates to a system which inserts human-readable text data into the video signal in response to operations performed on the video signal generating apparatus or on the camera attached thereto.

2. Description of the Related Art

[Original Purpose of the EssenceMark™]

SMPTE (Society of Motion Picture and Television Engineers) stipulates criteria called KLV (Key-Length-Value) as a basic structure in which to describe metadata. As shown in FIG. 1, metadata is described as a byte string of a Key-Length-Value structure. In this structure, "Key" is a 16-byte label indicative of a metadata type. All keys are registered in an SMPTE metadata dictionary. "Value" denotes an actual value of the metadata indicated by the key. "Length" preceding "Value" stands for the data length of "Value" (number of bytes).

The applicant of the present invention has proposed metadata called "EssenceMark" (registered trademark), referred to as EssenceMark™ hereunder. The metadata was devised as a variation of "Term Value," one of the KLV metadata types according to SMPTE and used as bookmarks of AV (audio video) materials. The proposed metadata is explained illustratively by Yoshiaki Shibata, Takumi Yoshida and Mitsutoshi Shinkai in "EssenceMark—SMPTE Standard-based Textual Video Marker," SMPTE Motion Imaging Journal Vol. 114, No. 12, pp. 463 to 473, December 2005 (Non-Patent Document 1), and in "EssenceMark," an article in the September 2006 issue of the Journal of the Motion Picture and Television Engineering Society of Japan Inc. (Non-Patent Document 2). The use of EssenceMark™ involves attaching human-readable text data directly or indirectly to desired frames of an AV material. The primary objective of EssenceMark™ is to provide high-speed access to desired locations in the material selectively according to text data values. Illustratively, a particular location furnished with EssenceMark™ is instantly accessed, or all frames with specific EssenceMark™ are extracted and displayed as thumbnails (as shown in FIG. 5 of the above-cited Non-Patent Document 2). The manner in which to store multi-byte characters such as those of the Japanese language using EssenceMark™ is precisely established.

SMPTE stipulates that for the baseband transmission of an AV material in SDI (Serial Digital Interface) format, KLV metadata packets are to be stored as ancillary data in VBI (vertical blanking interval) areas of the material (SMPTE 259M, 292M, 291M). As a variation of the KLV metadata, EssenceMark™ in SDI format is thus transmitted as ancillary data placed in the VBI areas of the frames to which the marker is attached.

Reserved words are part of the specifications of EssenceMark™. The words were first introduced as a common language to avert varying descriptions of the frequently used EssenceMark™ values (i.e., values shown in FIG. 1). FIG. 2 gives a list of the reserved words. Each reserved word begins with a symbol "_." For example, the word "_RecStart" is a reserved word that designates a recording start point of an AV material. Where videotapes are patched together for consecutive recording, the recording start location of each videotape may be marked by this reserved word. The word "_RecEnd" is a reserved word that designates a recording end point of the AV material. "_ShotMark1" and "_ShotMark2" are reserved words that specify points of interest of the AV material.

As EssenceMark™ values, any text data may be designated. Still, the most practical of the values are those offered as text values that have their own meanings. FIG. 3 is the same as FIG. 2 in the above-cited Non-Patent Document 1 (and equivalent to FIG. 1 in the above-cited Non-Patent Document 2), schematically showing an AV material (video clips) furnished with EssenceMark™. FIG. 4 is the same as FIG. 6 in the above-cited Non-Patent Document 1, showing a list of EssenceMark™ values in XML (Extensible Markup Language) attached to clip 1 in FIG. 3. This list of EssenceMark™ values attached to the AV material and expressed as a human-readable XML document gives an at-a-glance picture of typical frames furnished with particular EssenceMark™ values having their own meanings.

Generally, when video recording equipment (e.g., optical disk recorders, VCRs) is said to comply with EssenceMark™, that means the equipment is capable of simultaneously recording images and EssenceMark™ associated with the images. Earlier, this applicant proposed techniques for attaching text data such as EssenceMark™ to video materials as they are picked up and recorded in real time so that at a later stage, relevant image scenes furnished with the text data may be instantly accessed, displayed, or otherwise edited efficiently on an editing apparatus (see Japanese Patent Laid-Open No. 2003-299010). However, such video recording equipment is incapable of starting or stopping the recording of images in accordance with EssenceMark™ attached to video materials.

[Typical Endoscope (Camera) and Video Recording Apparatus]

At present, a medical endoscope (i.e., camera) is typically connected with a video recording apparatus (e.g., optical disk recorder, VCR) by use of two cables: a coaxial cable for transmitting image signals in HD-SDI format, and an RS232C cable for controlling the downstream video recording apparatus. This setup poses no problem when the camera and the video recording apparatus are connected on a peer-to-peer basis. Problems can arise if the two apparatuses constitute part of a larger system. For example, there may be a system that causes the moving images recorded by the video recording apparatus to be fed to a diagnostic program for analysis and allows the result of the analysis to be stored into a separate PACS (picture archiving and communication system for storage and distribution of clinical images). In this system, the video recording apparatus is obviously connected to a communication network. Whenever it is desired to view original moving images on a main monitor of the system, the image reproduction should be controlled by a personal computer carrying the diagnostic program in use; it is not practical to bring the camera up to the person who wants to view the images (it is assumed that the video recording apparatus is not at hand but controlled remotely). In other words, whereas the operations directly related to image pickup and recording are to be controlled by the camera, unrelated operations such as reproduction, fast-forward, rewind, and random access to desired locations should preferably be made through a separate interface and not from the camera.

Typical video recording apparatuses are designed to handle all control commands via the RS232C cable as mentioned above. This makes it difficult for any such apparatus to function as a subsystem in a larger system configuration. There could be provided at least two RS232C cables of which one may be used for the usual connection with the camera and the other for connection with the PC carrying the diagnostic program. Such a setup, however, would demand establishing new provisions regulating cases in which, illustratively, competing control commands are simultaneously input through these RS232C cables (the present protocol has no provisions against such contingencies). The arrangements involving the additional installation of redundant interface circuits will lead to considerable cost increase. Having to install the coaxial cable and the RS232C cable between the camera and the video recording apparatus is bothersome in the first place.

[Connection Between the Camera and the Video Recording Apparatus]

This applicant has filed another patent application (Japanese Patent Application No. 2005-77965), undisclosed at the time of this filing. The above application proposes a technique to be used as follows: there are cases where a plurality of broadcasting stations are represented by a single master station that picks up and records videos for coverage and distributes them to the other stations coming under the master station. In such cases, the proposed technique enables the video camera of the master station creating a material videotape to have the subordinate stations simultaneously create the same material videotape on their VCRs. Specifically, video signals transmitted by the video camera to at least one video recording apparatus connected to that video camera are multiplexed with control signals. The video recording apparatus or apparatuses under the master station detect control signals from the incoming video signals and control their internal video recording facilities accordingly.

However, the above-cited Patent Application makes use of values that are not meaningful by themselves (i.e., human-unreadable) as control information. Such human-unreadable information is stored in the user area (unstandardized and designed to accommodate user-specific specifications) of ancillary data packets according to SMPTE 291M. When placed in the user area, the human-unreadable information can only be interpreted correctly by the video recording apparatus complying with the proposed invention of the filed application. No other video recording apparatus is capable of determining what the information in the user area signifies. No interoperability exists between these apparatuses as per different specifications. The proposed invention thus has difficulty letting its embodiment materialize beyond the scope of apparatus-specific functional expansion.

According to the above-cited Patent Application, control information is limited to basic control commands (e.g., recording start, recording end, fast-forward, rewind) of the video recording apparatus. That is because what is intended is solely and precisely to execute such limited tasks as enabling the master video camera creating a material videotape to have the subordinate VCRs create the same material videotape simultaneously.

SUMMARY OF THE INVENTION

As described, there already exist techniques that utilize EssenceMark™ for instant access to scenes of interest and for listing of relevant scenes on an editing apparatus; techniques (yet to be disclosed) that provide video materials with human-unreadable information constituting basic control commands used on a video recording apparatus downstream of the video camera; and techniques that allow the camera such as an endoscope to control a video recording apparatus using a control cable apart from the video signal transmission cable (e.g., Japanese Patent Laid-Open No. 2004-305373).

However, there has yet to be proposed a technique that would attach to video materials human-readable information (i.e., meaningful by itself) in response to certain operations carried out on a camera or on an apparatus downstream thereof, so that the downstream apparatus might utilize the attached information for performance reflecting the operations. Nor has there been any proposed technique that would ensure interoperability between the apparatus transmitting video materials furnished with such human-readable information on the one hand, and another apparatus not complying with the technique and receiving the transmitted video materials on the other hand.

The present invention has been made in view of the above circumstances and provides arrangements that furnish video materials with information meaningful by itself in response to certain operations carried out on a camera or on an apparatus downstream thereof, so that the downstream apparatus may utilize the furnished information for performance reflecting the operations. The invention further envisages ensuring interoperability between an apparatus transmitting video materials furnished with such information according to the invention on the one hand, and another apparatus not embodying the invention but receiving the transmitted video materials on the other hand.

In carrying out the present invention and according to one embodiment thereof, there is provided a video signal generating apparatus including: a camera configured to generate a video signal; an operating device configured to operate at least either the camera or an apparatus configured to receive the video signal; a text data generating device configured to generate text data including a meaningful term in response to the operation performed on the operating device; and a text data inserting device configured to insert the text data generated by the text data generating device into the video signal in a corresponding manner.

Where the video signal generating apparatus of the present invention is in use, an operation performed by the operating device on either the camera or a downstream apparatus (i.e., video signal receiving apparatus) generates text data including a meaningful term (i.e., human-readable information). The generated text data is inserted into the video signal in a suitably corresponding manner.

When the text data containing a human-readable term is attached to a video material in accordance with the operation performed on the camera or the downstream apparatus as outlined above, the downstream apparatus can make use of the text data to effect a process reflecting that operation.

According to another embodiment of the present invention, there is provided a video signal receiving apparatus including: a receiving device configured to receive a video signal into which is inserted text data including a meaningful term; a text data extracting device configured to extract the text data from the video signal received by the receiving device; and an interpreting device configured to interpret as an operation instruction the text data extracted by the text data extracting device; wherein the video signal receiving apparatus performs the operation corresponding to the text data.

Where the video signal receiving apparatus of the present invention is in use, text data is first extracted from the received video signal. The extracted text data is interpreted as an operation instruction arranged to cause the apparatus to carry out an operation reflecting the text data. Upon receipt of the video signal generated by the inventive video signal generating apparatus, the video signal receiving apparatus of the invention thus performs an operation reflecting the operation executed on the upstream apparatus.

According to a further embodiment of the present invention, there is provided a video signal generating and receiving system made up of the above-described video signal generating apparatus and video signal receiving apparatus of the invention. The video signal generating apparatus inserts text data into the video signal which is then sent to and received by the video signal receiving apparatus.

Where the inventive video signal generating and receiving system is in use, an operation performed either on the camera of the video signal generating device or on the video signal receiving apparatus generates text data including a meaningful term. The generated text data is inserted into the video signal. The video signal together with the inserted text data is received by the video signal receiving apparatus. Using the text data upon signal reception, the video signal receiving apparatus performs a process reflecting the operation carried out on the video signal generating apparatus.

Preferably, where the video signal generating and receiving system of the present invention is in use, the camera of the video signal generating apparatus may generate a serial digital video signal in HD-SDI format stipulated by SMPTE; the text data generating device of the video signal generating apparatus may generate as the text data a term value (including EssenceMark™ as its variation) which is a type of metadata stipulated by SMPTE; the text data inserting device of the video signal generating apparatus may insert the term value as ancillary data into a vertical blanking interval of the serial digital video signal in the HD-SDI format; the receiving device of the video signal receiving apparatus may receive the serial digital video signal in the HD-SDI format; and the text data extracting device of the video signal receiving apparatus may extract the term value as the text data from an ancillary data area in the vertical blanking interval of the serial digital video signal in the HD-SDI format.

The text data containing such meaningful terms is inserted as standardized metadata into the video signal generated by the inventive video signal generating apparatus. Upon receipt of the video signal thus prepared by the video signal generating apparatus, a receiving apparatus other than the video signal receiving apparatus of the invention can interpret exactly what the included text data signifies. This ensures interoperability between these two apparatuses operating in tandem.

According to the video signal generating apparatus of the present invention, an operation performed on the camera or on the apparatus downstream thereof generates text data containing a meaningful term that is attached to the video material. The downstream apparatus then utilize the text data in executing a process reflecting that operation.

The video signal receiving apparatus of the present invention is arranged to receive the video signal generated by the inventive video signal generating apparatus. Using the text data extracted from the received video signal, the video signal receiving apparatus carries out a process reflecting the operation effected on the video signal generating apparatus.

According to the inventive video signal generating and receiving system made up of the video signal generating apparatus and video signal receiving apparatus, an operation performed on the camera of the video signal generating device or on the video signal receiving apparatus generates text data containing a meaningful term. Upon receipt of the video signal together with the text data, the video signal receiving apparatus makes use of the text data to carry out a process reflecting the operation effected on the video signal generating apparatus.

Preferably, the term value (including EssenceMark™ as its variation) which is a type of metadata stipulated by SMPTE may be inserted into the ancillary data area in the vertical blanking interval of the serial digital video signal in the HD-SDI format. In this case, a receiving apparatus other than the inventive video signal receiving apparatus can correctly determine how the metadata in question is to be utilized and what the inserted text data signifies. This guarantees interoperability between the two apparatuses being connected.

BRIEF DESCRIPTION OF THE DRAWINGS

FIG. 1 is a schematic view showing a structure of the KLV metadata stipulated by SMPTE;

FIG. 2 is a tabular view listing the reserved words of EssenceMark™;

DETAILED DESCRIPTION OF THE PREFERRED EMBODIMENTS

Preferred embodiments of the present invention will now be described in reference to the accompanying drawings.

The ensuing description will focus primarily on how the invention is embodied illustratively in the form of an electronic endoscope for medical purposes and an optical disk recorder for recording images picked up by the electronic endoscope.

Figure 5:
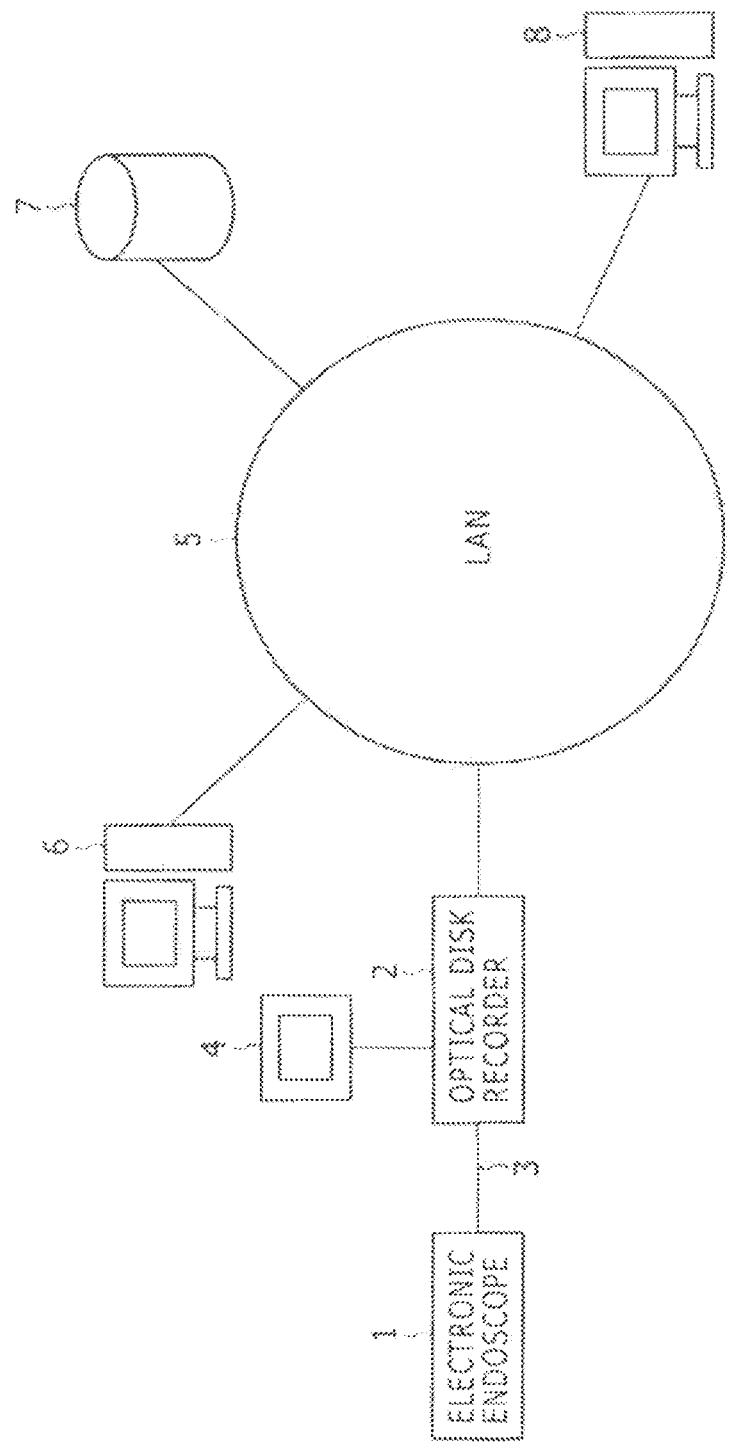
FIG. 5 is a schematic view showing an overall configuration of a medical video network system.

FIG. 5 outlines a typical configuration of a medical video network system including the above-mentioned electronic endoscope and optical disk recorder. The electronic endoscope 1 and optical disk recorder 2 are connected by a coaxial cable 3 that transmits a serial digital video signal in HD-SDI format according to the SMPTE 292M standard (the signal will be referred to as the HD-SDI signal hereunder). A video display monitor 4 is connected to the optical disk recorder 2.

The optical disk recorder 2 is also connected to a diagnostic PC (personal computer carrying diagnostic software) 6, an archive system (PACS: picture archiving and communication system for storage and distribution of clinical images) 7, and an electronic clinical chart system 8 by way of a LAN (local area network) 5 inside the medical facilities.

Figure 6:
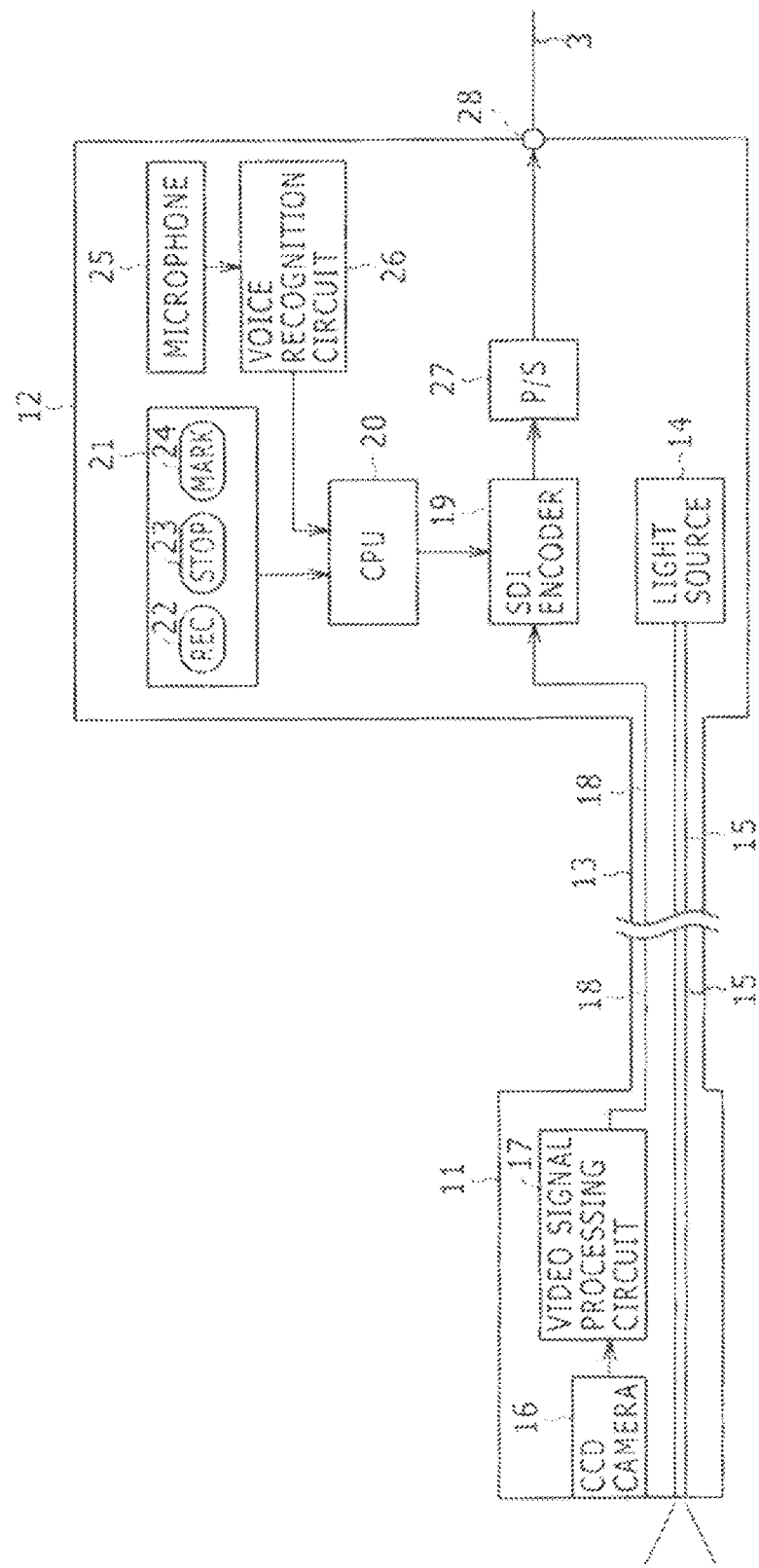
FIG. 6 is a block diagram showing a structure of an electronic endoscope as part of the configuration in FIG. 5.

FIG. 6 is a block diagram showing a structure of the electronic endoscope 1. The electronic endoscope 1 is made up of a scope unit (camera) 11 to be inserted into the human body and a processor unit 12, the two units being connected by an elastic tube 13. Light from a light source 14 inside the processor unit 12 is guided through a light guide 15 inside the tube 13 and emitted from a tip of the scope unit 11. Using this lighting, a CCD camera (image pickup lens and CCD imaging device) 16 at the tip of the scope unit 11 takes pictures inside the human body.

An image pickup signal generated photoelectrically by the CCD camera 16 is forwarded to a video signal processing circuit 17 inside the scope unit 11. The video signal processing circuit 17 subjects the image pickup signal to digital conversion and various other signal processes (luminance signal process, color signal process, gamma correction, conversion to Y/Cb/Cr, etc.) thereby generating a digital HDTV signal. The digital HDTV signal thus generated is sent to an SDI encoder 19 in the processor unit 12 through a parallel cable 18 inside the tube 13.

The SDI encoder 19 is a circuit that effects multiplexing, scrambling and other processes on the digital HDTV signal in accordance with the SMPTE 292M standard (HD-SDI). Under control of a CPU 20 supervising the entire processor unit 12, the SDI encoder 19 superimposes EssenceMark™ as ancillary data onto a VBI (vertical blanking interval) area of the digital HDTV signal according to the SMPTE 292M standard.

As one feature of the present invention, a control panel 21 on the housing surface of the processor unit 12 includes a "REC" button 22, a "STOP" button 23, and a "MARK" button 24 used to operate the optical disk recorder 2 (FIG. 1). A microphone 25 is mounted close to the control panel 21 on the housing surface of the processor unit 12.

The "REC" button 22 is a button which, when operated, causes the optical disk recorder 2 to start video recording. The "STOP" button 23, when operated, causes the optical disk recorder 2 to stop the ongoing video recording.

The "MARK" button 24 is operated to mark a video frame of interest (e.g., a frame showing the affected region of a patient). The button operation causes the optical disk recorder 2 to capture the frame in question as a still image.

The microphone 25 allows the operator pronouncing illustratively the word "rec," "stop," or "mark" to replace the physical operation of the "REC" button 22, "STOP" button 23, or "MARK" button 24, respectively. A voice signal input to the microphone 25 is converted to an electrical signal that is sent to a voice recognition circuit 26. The voice recognition circuit 26 recognizes the pronounced word "rec," "stop," or "mark" and informs the CPU 20 of the result of the recognition.

Figures 7, 8:
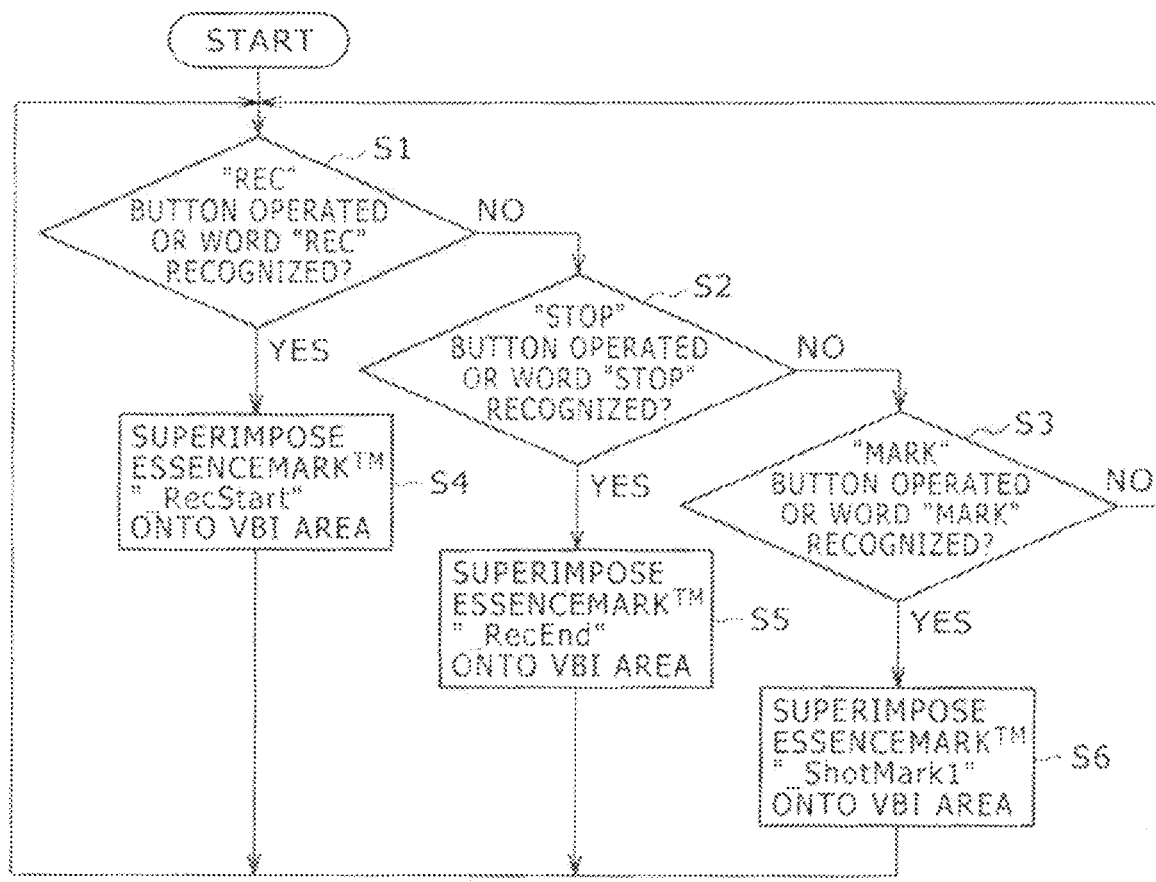
FIG. 7 is a flowchart of steps constituting a procedure by which the CPU in the electronic endoscope controls an SDI encoder.
FIG. 8 is a schematic view showing the EssenceMark™ value of "_RecStart"

FIG. 7 is a flowchart of steps constituting a typical procedure by which the CPU 20 controls the SDI encoder 19 on the basis of the operations performed on the "REC" button 22, "STOP" button 23, and "MARK" button 24 and in accordance with the result of the recognition by the voice recognition circuit 26.

When this procedure is started, checks are repeated in three steps until any one of them results in the affirmative. More specifically, a check is first made in step S1 to determine if the "REC" button 22 is operated or if the pronounced word "rec" is recognized by the voice recognition circuit 26. If the result of the check in step S1 is negative, then step S2 is reached. In step S2, a check is made to see if the "STOP" button 23 is operated or if the pronounced word "stop" is recognized by the voice recognition circuit 26. If the result of the check in step S2 is also negative, then step S3 is reached and a check is made to see if the "MARK" button 24 is operated or if the pronounced word "mark" is recognized by the voice recognition circuit 26. If the result of the check in step S3 is negative, then step S1 is reached again and the process is repeated.

If the result of the check in step S1 is affirmative, then step S4 is reached. In step S4, the CPU generates EssenceMark™ having the value (i.e., "Value" field of the KLV metadata in FIG. 1) representative of "_RecStart" (i.e., a reserved word indicating the recording start point of an AV material as shown in FIG. 2). The CPU 20 then controls the SDI encoder 19 to superimpose the generated EssenceMark™ as ancillary data onto the VBI area of the frame in effect at this timing. From step S4, control is returned to step S1.

If the result of the check in step S2 is affirmative, then step S5 is reached. In step S5, the CPU generates EssenceMark™ having the value representative of "_RecEnd" (i.e., a reserved word indicating the recording end point of the AV material as shown in FIG. 2). The CPU 20 then controls the SDI encoder 19 to superimpose the generated EssenceMark™ as ancillary data onto the VBI area of the frame in effect at this timing. From step S5, control is returned to step S1.

If the result of the check in step S3 is affirmative, then step S6 is reached. In step S6, the CPU generates EssenceMark™ having the value representative of "_ShotMark1" (i.e., a reserved word indicating a scene as a point of interest in the AV material as shown in FIG. 2). The CPU 20 then controls the SDI encoder 19 to superimpose the generated EssenceMark™ as ancillary data onto the VBI area of the frame in effect at this timing. From step S6, control is returned to step S1.

According to the procedure of FIG. 7 executed by the CPU 20, the SDI encoder 19 superimposes EssenceMark™ values onto the VBI area of the digital HDTV signal. FIG. 8 is a schematic view showing the EssenceMark™ value of "_RecStart" as an example of EssenceMark™ superimposed by the SDI encoder (in step S4 of FIG. 7). FIG. 8 is the same as FIG. 5 in the above-cited Non-Patent Document 1.

As shown in FIG. 6, a parallel digital video signal processed by the SDI encoder 19 is converted to a serial signal by a parallel/serial conversion circuit 27. This serial digital video signal (i.e., HD-SDI signal) is output from an HD-SDI output terminal 28 and sent to the optical disk recorder 2 (FIG. 5) through the coaxial cable 3 shown in FIG. 5.

Figure 9:
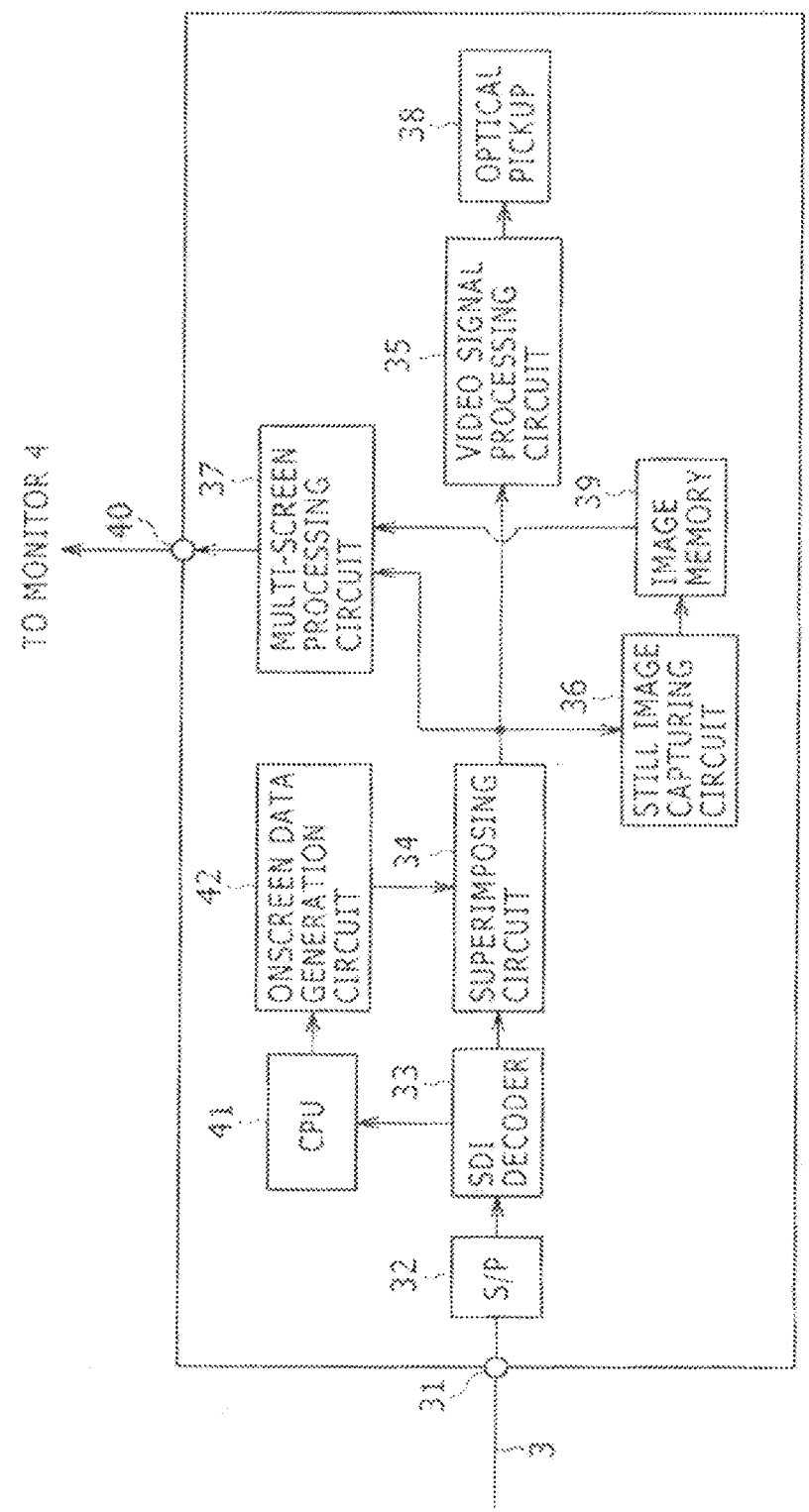
FIG. 9 is a block diagram showing a structure of an optical disk recorder as part of the configuration in FIG. 5.

FIG. 9 is a block diagram showing that portion of the optical disk recorder 2 which is relevant to the present invention. The HD-SDI signal sent through the coaxial cable 3 is input to an HD-SDI input terminal 31. The input HD-SDI signal is converted to a parallel signal by a serial/parallel conversion circuit 32 before being forwarded to an SDI decoder 33.

The SDI decoder 33 is a circuit that submits the converted parallel HD-SDI signal to such processes as descrambling and demultiplexing in order to restore the original digital HDTV signal. Furthermore, the SDI decoder 33 detects timing reference signals (EAV and SAV) and ancillary data from the VBI area of the digital HDTV signal.

The digital HDTV signal restored by the SDI decoder 33 is forwarded through a superimposing circuit 34 (for superimposing characters) to three circuits: a video signal processing circuit 35 for recording purposes, a still image capturing circuit 36, and a multi-screen processing circuit 37.

The video signal processing circuit 35 subjects the digital HDTV signals to such processes as addition of error-correcting code, conversion to a signal format suitable for recording onto optical disks, and data compression. The signal processed by the video signal processing circuit 35 is sent to an optical pickup 38.

The still image capturing circuit 36 captures still images from the digital HDTV signal. The data of each still picture thus captured is stored into an image memory 39 as an image file in DICOM (Digital Imaging and Communication in Medicine) format, which is a format for clinical image data.

The multi-screen processing circuit 37 generates a multi-screen video signal that arrays, on a single screen in reduced form, the digital HDTV signal from the superimposing circuit 34 and the still image data of image files (e.g., a predetermined number of the most recently created files) retrieved from the image memory 39. If no image file is found in the image memory 39, the multi-screen processing circuit 37 outputs in unmodified form the digital HDTV signal from the superimposing circuit 34 (alternatively, it is possible to generate a multi-screen video signal with its still image data portion left blank). The video signal generated by the multi-screen processing circuit 37 is output from a monitor display video output terminal 40 and sent to the monitor 4 in the configuration of FIG. 5.

The timing reference signals and ancillary data detected by the SDI decoder 33 are forwarded to a CPU 41 that controls the optical disk recorder 2 as a whole. Based on a time code in the ancillary data, the CPU 41 controls an onscreen data generation circuit 42 to generate onscreen data (characters) indicating the current time code. The characters generated by the onscreen data generation circuit 42 are sent to the superimposing circuit 34 whereby the characters are superimposed onto the digital HDTV signal.

The CPU 41 checks for the presence and type of EssenceMark™ in each frame of the ancillary data coming from the SDI decoder 33. The CPU 41 carries out the checks using the procedure shown in FIG. 10.

When this procedure is started, the checks are repeated in three steps until any one of them results in the affirmative. More specifically, a check is first made in step S11 to determine if the ancillary data of a given frame contains EssenceMark™ having the value (i.e., "Value" field of the KLV metadata in FIG. 1) representative of "_RecStart" (i.e., a reserved word indicating the recording start point of an AV material as shown in FIG. 2). If the result of the check in step S11 is negative, then step S12 is reached. In step S12, a check is made to see if the ancillary data of the frame contains EssenceMark™ having the value representative of "_RecEnd" (i.e., a reserved word indicating the recording end point of the AV material as shown in FIG. 2). If the result of the check in step S12 is also negative, then step S13 is reached and a check is made to see if the ancillary data of the frame contains EssenceMark™ having the value representative of "_ShotMark1" (i.e., a reserved word indicating a scene as a point of interest in the AV material as shown in FIG. 2). If the result of the check in step S13 is negative, then step S11 is reached again and the process is repeated.

If the result of the check in step S11 is affirmative, then step S14 is reached. In step S14, the CPU 41 controls the onscreen data generation circuit 42 (FIG. 9) to generate suitable characters such as "REC" indicating that video recording is underway for this and subsequent frames. In step S15, the CPU 41 controls an actuator for positioning the optical pickup 38 (FIG. 9) and a drive circuit (not shown) for driving a spindle motor to start video recording onto an optical disk (not shown) loaded in the optical disk recorder 2. This completes the processing on the current frame.

If the result of the check in step S12 is affirmative, then step S16 is reached. In step S16, the CPU 41 controls the onscreen data generation circuit 42 to stop generating the characters indicating that video recording is underway (i.e., characters generated in step S14 for the preceding frames). In step S17, the CPU 41 controls the actuator and the drive circuit to stop the ongoing video recording onto the optical disk. This completes the processing on the current frame.

Figures 3, 4:
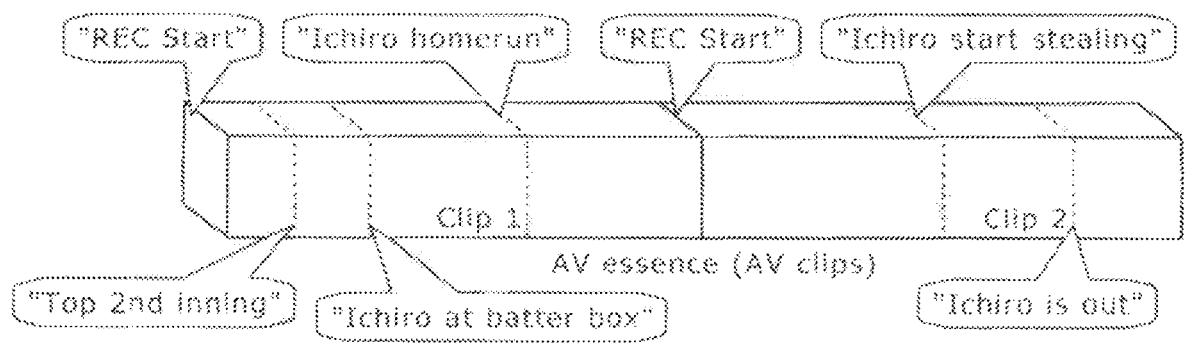
FIG. 3 is a schematic view showing video clips furnished with EssenceMark™.
FIG. 4 is a tabular view of an XML document made up of the EssenceMark™ values shown in FIG. 3.

If the result of the check in step S13 is affirmative, then step S18 is reached. In step S18, the CPU 41 stores the EssenceMark™ value "_ShotMark1" into an internal memory of the CPU 41 as a document file such as an XML document shown in FIG. 4, along with identification information (e.g., frame number) identifying the current frame. In step S19, the CPU 41 controls the still image capturing circuit 36 (FIG. 9) to capture a still image of the current frame and to store the captured image as an image file into the image memory 39. This completes the processing on the current frame.

What follows is a description of how images are recorded to the optical disk recorder 2 or are displayed on the monitor 4 in response to the operations performed on the electronic endoscope 1 in FIG. 5.

When the operator starts picking up images by operating the electronic endoscope 1, an HD-SDI signal is sent from the endoscope 1 to the optical disk recorder 2 through the coaxial cable 3. From the optical disk recorder 2, the HD-SDI signal is forwarded to the monitor 4. The images being picked up are displayed on the monitor 4 in this manner.

To get the optical disk recorder 2 to start recording images, the operator may either push the "REC" button 22 (FIG. 6) on the control panel 21 of the electronic endoscope 1 or pronounce the word "rec" toward the microphone 25 (FIG. 6) mounted close to the control panel 21. At this point, EssenceMark™ having the value of "_RecStart" is superimposed onto the VBI area of the HD-SDI signal (in step S4 of FIG. 7).

Figure 10:
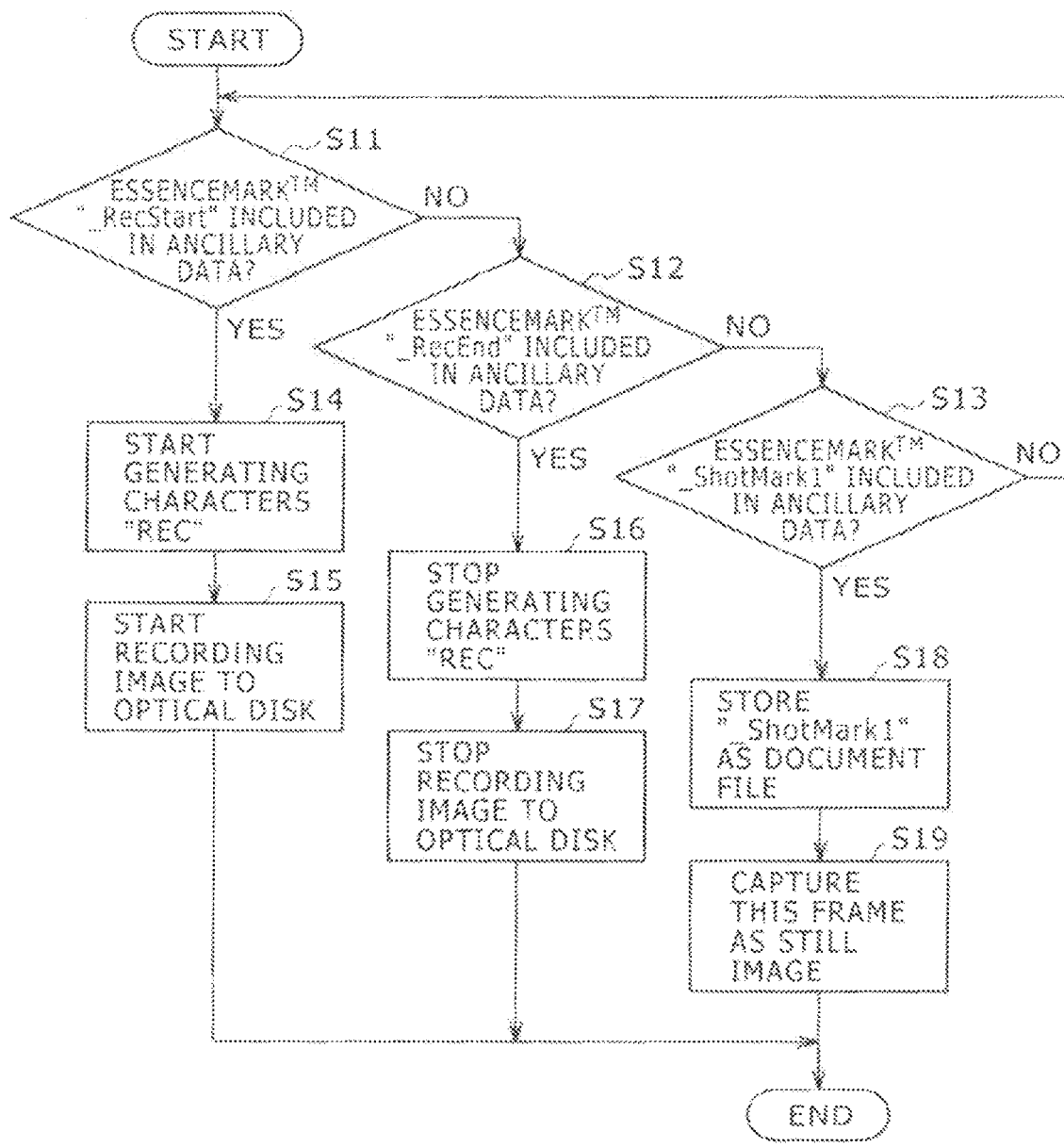
FIG. 10 is a flowchart of steps constituting a procedure carried out by the CPU in the optical disk recorder in accordance with EssenceMark™ values.

The optical disk recorder 2 separates this EssenceMark™ from the signal, interprets its value as an operation instruction, and starts recording images accordingly (in step S15 of FIG. 10). At the same time, suitable characters such as "REC" indicating that recording is underway is superimposed onto the recorded images. The characters are also shown superimposed on the display of the monitor 4.

With the video recording thus started, the operator may either operate the "MARK" button 24 on the control panel

21 (FIG. 6) or pronounce the word "mark" toward the microphone 25 upon viewing a frame of interest (e.g., a frame showing the affected region of a patient). At this point, EssenceMark™ having the value of "_ShotMark1" is superimposed onto the VBI area of the HD-SDI signal (in step S6 of FIG. 7).

The optical disk recorder 2 separates this EssenceMark™ from the signal, interprets its value as an operation instruction, and stores "_ShotMark1" as a document file together with the frame number (in step S18 of FIG. 10). The image of the frame is captured as a still image (in step S19 of FIG. 10). At the same time, the captured still image is shown on a multi-screen display of the monitor 4 together with the image being picked up.

Figure 11:
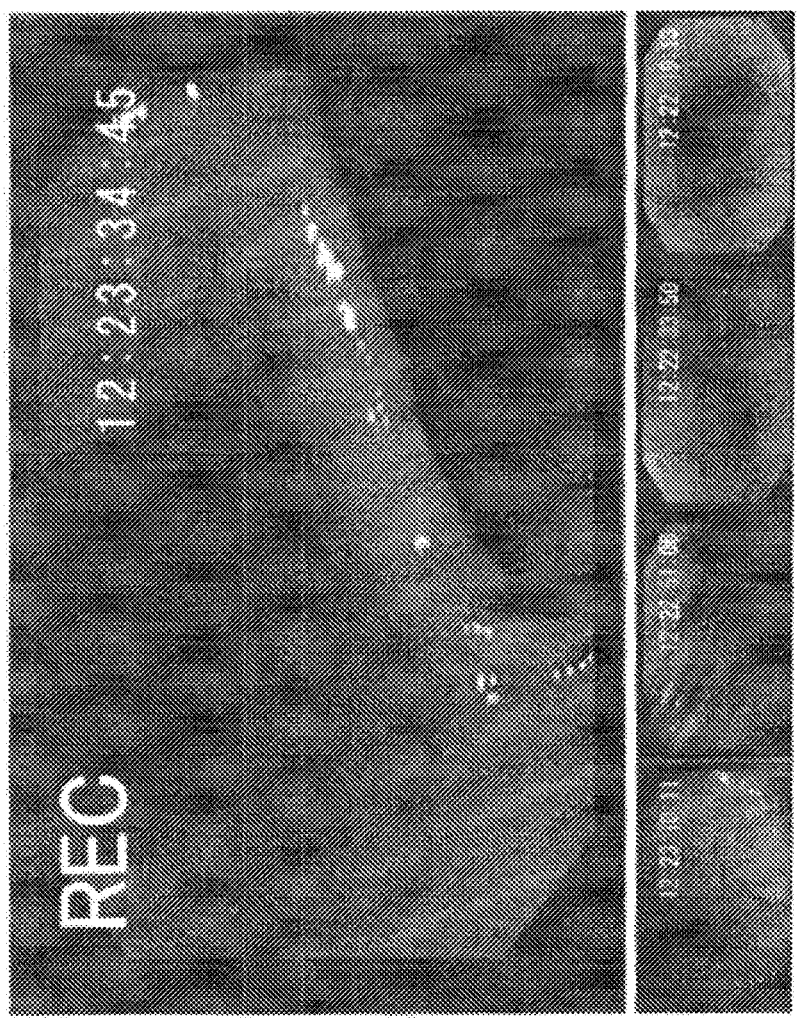
FIG. 11 is a schematic view of an onscreen display on a monitor as part of the configuration in FIG. 5.

FIG. 11 shows an onscreen display of the monitor 4 in effect when the "MARK" button 24 is pushed (or the word "mark" is pronounced) over a plurality of frames. The upper part of the screen displays the image being currently picked up. On this image, the current time code and the characters "REC" indicating that recording is underway are shown superimposed. The lower part of the screen displays four still images, arrayed chronologically from left to right (i.e., the time code on the leftmost image is closest to the current time code).

Thereafter, the operator may either push the "STOP" button 23 on the control panel 21 (FIG. 6) or pronounce the word "stop" toward the microphone 25 so as to stop the ongoing video recording by the optical disk recorder 2. At this point, EssenceMark™ having the value of "_RecEnd" is superimposed onto the VBI area of the HD-SDI signal (in step S5 of FIG. 7).

The optical disk recorder 2 separates this EssenceMark™ from the signal, interprets its value as an operation instruction, and stops the ongoing video recording accordingly (in step S17 of FIG. 10). Generation of the characters indicating the ongoing recording is stopped (in step S16 of FIG. 10), and the characters are no longer shown superimposed on the monitor 4.

As described, operations are carried out (physically or phonetically) on the control panel 21 of the electronic endoscope 1 to have the optical disk recorder 2 start video recording, capture still images, and stop the recording. In turn, the HD-SDI signal having EssenceMark™ as text data containing the corresponding meaningful terms is sent to and received by the optical disk recorder 2. Using the EssenceMark™ text data, the optical disk recorder 2 starts video recording, captures still images, and stops the recording reflecting the operations performed on the electronic endoscope 1.

Simply connecting the electronic endoscope 1 with the optical disk recorder 2 by a single coaxial cable 3 for HD-SDI signal transmission makes it possible for the endoscope to control the recorder in recording and still image capturing.

The electronic endoscope 1 controls the optical disk recorder 2 in video recording operation but does not control reproduction of recorded images. The reproduction of recorded images is controlled illustratively by the diagnostic PC 6 (FIG. 5) via the LAN 5. Under control of the diagnostic PC 6, the optical disk recorder 2 may have its recorded images put into files and sent out by way of the LAN 5. With these arrangements in place, the system made up of the electronic endoscope 1 and optical disk recorder 2 may be set up as a subsystem of the medical video network system in FIG. 5 operating as a host system.

Since EssenceMark™ is human-readable text data as a variation of the standardized KLV metadata, an apparatus not embodying the present invention such as the optical disk recorder 2 receiving the HD-SDI signal from the electronic endoscope 1 can correctly determine how the metadata in question is to be utilized and what the text data signifies. This guarantees interoperability between the connected apparatuses (for example, upon reproduction following the recording of images, it is possible to display a list of thumbnail images each having the EssenceMark™ value of "_ShotMark1" superimposed thereon).

Figure 12:
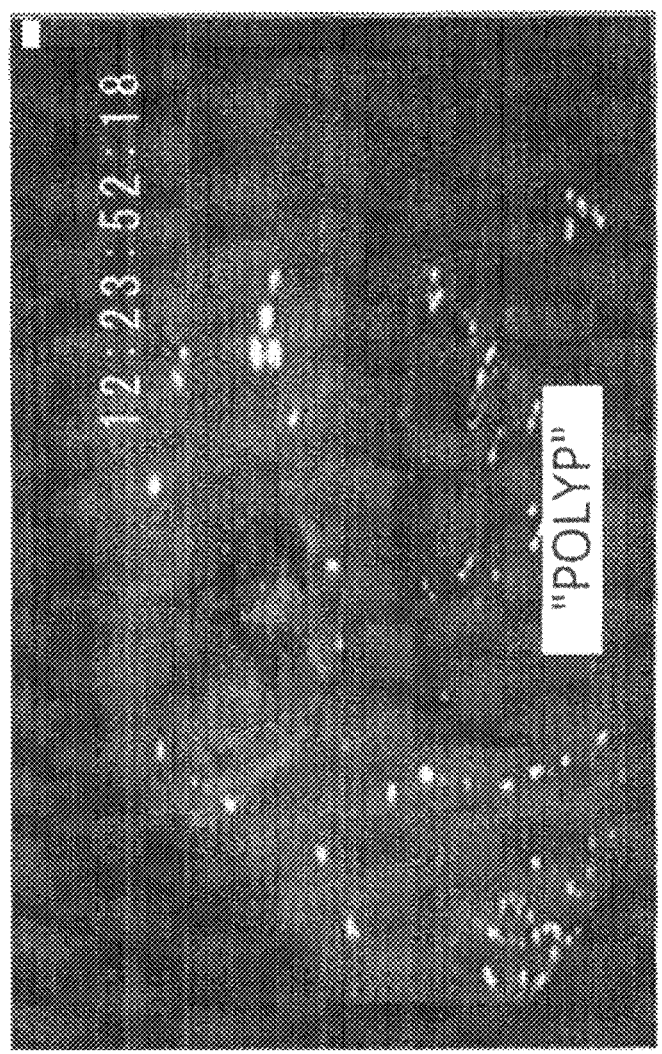
FIG. 12 is a schematic view of a variation of the onscreen display on the monitor.

The foregoing examples have shown that the EssenceMark™ values of the reserved words listed in FIG. 2 are generated and superimposed on the HD-SDI signal. Alternatively, an EssenceMark™ value other than those of the reserved words may be suitably named (e.g., with disease name such as "polyp") and assigned to an additional control button on the control panel 21 of the electronic endoscope 1. Operating this control button generates the EssenceMark™ value assigned to the button and causes the generated EssenceMark™ value to be superimposed onto the HD-SDI signal. The optical disk recorder 2, for its part, causes the onscreen data generation circuit 42 to generate the characters corresponding to the received EssenceMark™ value. This allows the resulting image, with the EssenceMark™ value ("POLYP" in FIG. 12) superimposed thereon, to be recorded onto the optical disk recorder 2 and displayed on the monitor 4 at the same time, as shown in FIG. 12.

As another alternative, the control panel 21 may be furnished with additional buttons for setting the time period in which to display the superimposed name in characters, the locations at which to display the name, and the font color in which to display these characters. A command indicating these settings may be added to the EssenceMark™ value in a manner distinct from the superimposed name. Given the command, the optical disk recorder 2 may establish accordingly the time period in which to display the superimposed characters, the locations at which to display the characters, and the font color in which to display the characters.

In the foregoing examples, the EssenceMark™ values were shown to be generated and superimposed by physically operated buttons or by phonetically input words. Alternatively, an EssenceMark™ value may be generated and superimposed using one of the following three events as a trigger:

(1) a predetermined result is obtained through image processing (e.g., the patient's affected region is detected by application of pattern recognition techniques);

(2) a predetermined result is obtained through voice processing whereby both image and voice are recorded (e.g., voice of a predetermined level is detected); or (3) a preset time is reached.

In the foregoing examples, the present invention was shown to be applied to the electronic endoscope for medical purposes and to the optical disk recorder for recording images picked up by the electronic endoscope. Alternatively, the present invention may be applied to varieties of applications covering security (crime and disaster prevention), academic pursuits (excavation of ancient ruins), and any other field where images generated by a camera are recorded by another apparatus. Furthermore, where images picked up by a camera-equipped apparatus are received by another apparatus having no capability of video recording, this invention may be utilized to control the latter apparatus in its operation.

In the foregoing examples, the EssenceMark™ values were shown to be generated and superimposed in response to the operations carried out on the electronic endoscope 1 with regard to the optical disk recorder 2.

Alternatively, where the invention is applied to an apparatus having a control unit that operates a camera, EssenceMark™ values may be generated and superimposed in response to the operations performed on the camera. For example, when the camera is operated to change its filter setting, shutter speed or gain setting, the reserved word "_FilterChange," "_ShutterSpeedChange" or "_GainChange" as part of those shown in FIG. 2 may be generated and superimposed as the corresponding EssenceMark™ value.

In the foregoing examples, EssenceMark™ text data was shown generated and superimposed onto the VBI area of the HD-SDI signal. Alternatively, it is possible to generate text data with meaningful words other than those of EssenceMark™, and to superimpose such text data onto video signals in a format other than that of the HD-SDI signal.

It should be understood by those skilled in the art that various modifications, combinations, sub-combinations and alterations may occur depending on design requirements and other factor in so far as they are within the scope of the appended claims or the equivalents thereof.

What is claimed is:

1. A medical video recorder comprising circuitry configured to:
   receive an endoscopic video signal with a generated metadata added to the endoscopic video signal;
   interpret the generated metadata; and
   process the endoscopic video signal based on the interpreted metadata,
   wherein processing the endoscopic video signal includes the circuitry being further configured to start recording the endoscopic video signal in the video recorder in response to the interpreted metadata, and
   wherein the generated metadata added to the endoscopic video signal includes at least one of a record start, a record end, or a point of interest generated in response to an input operation performed by an operator of an endoscope generating the endoscopic video signal.

2. The medical video recorder according to claim 1, wherein the endoscopic video signal is a serial digital video signal in HD-SDI format stipulated by SMPTE, and
   wherein the metadata is a term value; which is a type of metadata stipulated by SMPTE, inserted as ancillary data into a vertical blanking interval of the endoscopic video signal in the HD-SDI format.

3. The medical video recorder according to claim 1, wherein the endoscopic video signal includes text data designating a video recording start point and a video recording end point in response to the execution of the recording start executor and the recording end executor respectively.

4. The medical video recorder according to claim 1, wherein a frame is identified as a video frame of interest in response to an input operation by an operator.

5. The medical video recorder according to claim 1, wherein the circuitry is further configured to:
   recognize an object based on processing of the endoscopic video signal; and
   determine the generated metadata in response to a result of the object recognition.

6. The medical video recorder according to claim 1, wherein the generated metadata is included as ancillary data in the endoscopic video signal,
   wherein the circuitry is further configured to:
   determine if the generated metadata is present in the ancillary data of the endoscopic video signal;
   if so, determine a text data designation included in the generated metadata present in the ancillary data; and
   cause a display to present the determined text data designation in combination with video data included in the endoscopic video signal.

7. The medical video recorder according to claim 6, where the text data designation is one of recording start, recording end, a point of interest, or a time.

8. A method of operating medical video recorder comprising:
   receiving an endoscopic video signal with a generated metadata added to the endoscopic video signal;
   interpreting the generated metadata; and
   processing the endoscopic video signal based on the interpreted metadata,
   wherein processing the endoscopic video signal includes starting to recording the endoscopic video signal in the video recorder based on in response to the interpreted metadata, and
   wherein the generated metadata added to the endoscopic video signal includes at least one of a record start, a record end, or a point of interest generated in response to an input operation performed by an operator of an endoscope generating the endoscopic video signal.

9. The method according to claim 8, wherein the endoscopic video signal is a serial digital video signal in HD-SDI format stipulated by SMPTE, and
   wherein the metadata is a term value, which is a type of metadata stipulated by SMPTE, inserted as ancillary data into a vertical blanking interval of the endoscopic video signal in the HD-SDI format.

10. The method according to claim 8, wherein the endoscopic video signal includes text data designating a video recording start point and a video recording end point in response to the execution of the recording start executor and the recording end executor respectively.

11. The method according to claim 8, wherein a frame is identified as a video frame of interest in response to an input operation by an operator.

12. The method according to claim 8, further comprising:
    recognizing an object based on processing of the endoscopic video signal; and
    determining the generated metadata in response to a result of the object recognition.

13. The method according to claim 8, wherein the generated metadata is included as ancillary data in the endoscopic video signal, the method further comprising:
    determining if the generated metadata is present in the ancillary data of the endoscopic video signal;
    if so, determining a text data designation included in the generated metadata present in the ancillary data; and
    causing a display to present the determined text data designation in combination with video data included in the endoscopic video signal.

14. The method according to claim 13, where the text data designation is one of recording start, recording end, a point of interest, or a time.

15. A medical video network system comprising an endoscope and a medical video recorder, the medical video recorder comprising circuitry configured to:
    receive an endoscopic video signal from the endoscope with a generated metadata added to the endoscopic video signal;
    interpret the generated metadata; and
    process the endoscopic video signal based on the interpreted metadata, wherein processing the endoscopic video signal includes the circuitry being further configured to start to record the endoscopic video signal in the video recorder in response to the interpreted metadata, and wherein the generated metadata added to the endoscopic video signal includes at least one of a record start, a record end, or a point of interest generated in response to an input operation performed by an operator of an endoscope generating the endoscopic video signal.

16. The medical video network system according to claim 15, wherein the endoscopic video signal is a serial digital video signal in HD-SDI format stipulated by SMPTE, and wherein the metadata is a term value, which is a type of metadata stipulated by SMPTE, inserted as ancillary data into a vertical blanking interval of the endoscopic video signal in the HD-SDI format.

17. The medical video network system according to claim 15, wherein the endoscope includes circuitry configured to include text data designating a video recording start point and a video recording end point in the endoscopic video signal in response to the execution of the recording start executor and the recording end executor respectively.

18. The medical video network system according to claim 15, wherein the endoscope includes circuitry configured to:

identify a frame as a video frame of interest in response to an input operation to the endoscope by an operator; and include a point of interest in the generated metadata designated in the endoscopic video signal in response to an input operation performed by the operator of the endoscope.

19. The medical video network system according to claim 15, wherein the circuitry of the medical video recorder is further configured to:

recognize an object based on processing of the endoscopic video signal; and determine the generated metadata in response to a result of the object recognition.

20. The medical video network system according to claim 15, wherein circuitry of the endoscope is further configured to include the generated metadata as ancillary data in the endoscopic video signal, and wherein the circuitry of the medical video recorder is further configured to:

determine if the generated metadata is present in the ancillary data of the endoscopic video signal;

if so, determine a text data designation included in the generated metadata present in the ancillary data; and cause a display to present the determined text data designation in combination with video data included in the endoscopic video signal.

\* \* \* \* \*